US009333156B2

(12) United States Patent
Ito (10) Patent No.: US 9,333,156 B2
(45) Date of Patent: May 10, 2016

(54) EXTERNAL PREPARATION FOR SKIN (75) Inventor: Yoshiyasu Ito, Tokyo (JP)

(73) Assignee: SBI Pharmaceuticals Co., Ltd., Tokyo (JP)

( * ) Notice: Subject to any disclaimer, the term of this patent is extended or adjusted under 35 U.S.C. 154(b) by 0 days.

(21) Appl. No.: 12/945,177

(22) Filed: Nov. 12, 2010

(65) Prior Publication Data
US 2011/0060042 A1 Mar. 10, 2011

Related U.S. Application Data (62) Division of application No. 11/912,433, filed as application No. PCT/JP2005/017681 on Sep. 27, 2005, now abandoned.

(30) Foreign Application Priority Data

Apr. 28, 2005 (JP) ................. 2005-131171

(51) Int. Cl.
A61K 8/44 (2006.01)
A61K 9/00 (2006.01)
A61K 31/197 (2006.01)
A61K 31/295 (2006.01)
A61K 33/26 (2006.01)
A61Q 19/00 (2006.01)
A61Q 19/02 (2006.01)
A61Q 19/08 (2006.01)
A61K 31/17 (2006.01)
A61K 47/10 (2006.01)

(52) U.S. Cl.
CPC ............. *A61K 8/44* (2013.01); *A61K 9/0014* (2013.01); *A61K 31/17* (2013.01); *A61K 31/197* (2013.01); *A61K 31/295* (2013.01); *A61K 33/26* (2013.01); *A61Q 19/00* (2013.01); *A61Q 19/007* (2013.01); *A61Q 19/02* (2013.01); *A61Q 19/08* (2013.01); *A61K 47/10* (2013.01); *A61K 2800/88* (2013.01)

(58) Field of Classification Search
None
See application file for complete search history.

(56) References Cited

U.S. PATENT DOCUMENTS

| | | | |
|---|---|---|---|
| 4,259,318 A | | 3/1981 | Duhé et al. |
| 5,520,905 A * | | 5/1996 | Uhlmann et al. ............ 424/59 |
| 5,605,933 A * | | 2/1997 | Duffy et al. ............... 514/557 |
| 6,114,389 A * | | 9/2000 | Bouras ...................... 514/574 |
| 6,372,234 B1 | | 4/2002 | Deckers et al. |
| 6,911,194 B2 | | 6/2005 | Moan et al. |
| 2002/0064540 A1* | | 5/2002 | Allec et al. ................ 424/401 |
| 2003/0133888 A1 | | 7/2003 | Moan et al. |
| 2003/0212127 A1 | | 11/2003 | Glassman et al. |
| 2004/0043085 A1 | | 3/2004 | Mautone et al. |
| 2005/0031547 A1* | | 2/2005 | Tamarkin et al. ............. 424/45 |
| 2005/0123620 A1* | | 6/2005 | Chiou ....................... 424/603 |
| 2005/0170007 A1 | | 8/2005 | Kuklinski et al. |
| 2007/0249721 A1 | | 10/2007 | Ito |

FOREIGN PATENT DOCUMENTS

| | | |
|---|---|---|
| AT | 410 633 B | 6/2003 |
| EP | 1 238 652 A1 | 9/2002 |
| EP | 1312353 A1 | 5/2003 |
| EP | 1 413 303 A1 | 4/2004 |
| JP | 58152805 | 9/1983 |
| JP | 2003-040770 | 2/1990 |
| JP | 2002-020294 | 4/1990 |
| JP | 04-009360 | 1/1992 |
| JP | 2000-290135 | 1/1995 |
| JP | H07-053487 | 2/1995 |
| JP | H08-081322 | 3/1996 |
| JP | 11-116446 A | 4/1999 |
| JP | H11-116446 | 4/1999 |
| JP | 02-056409 | 10/2000 |
| JP | 2000-281556 | 10/2000 |
| JP | 2001-172154 A | 6/2001 |
| JP | 07-010750 | 1/2002 |
| JP | 2002-179518 A | 6/2002 |
| JP | 02-108612 | 2/2003 |
| JP | 2004-284962 | 10/2004 |
| WO | WO 01/85125 | 11/2001 |
| WO | WO 02/053122 A2 | 7/2002 |
| WO | WO 03/011275 | 2/2003 |

OTHER PUBLICATIONS

Sun and Skin . . . An Unhealth Partnership, Alliance for Aging Research (2003).*
English languge translation of JP 2694756 B (2012), pp. 1-7.*
India Patent Office Official Action dated Mar. 14, 2011 in corresponding Indian patent application 7765/DELNP/2007.
K. Lang et al., "Aminolevulinic Acid (Levulan®) in Photodynamic Therapy of Actinic Keratoses", Skin Therapy Letter, vol. 6 (10), Sep. 2001.
English Translation of the International Preliminary Report on Patentability. Written opinion of the International Searching Authority in corresponding International Application No. PCT/JP2005/017681, (2007).
International Search Report in PCT/JP2005/017681 (Completion Date: Oct. 31, 2005; Mailing Date: Nov. 5, 2005).
Examination Report Issued in related New Zealand Patent Application No. 562874 (Mailed Apr. 18, 2008).

(Continued)

Primary Examiner — Abigail Fisher
Assistant Examiner — Frank Choi
(74) Attorney, Agent, or Firm — Locke Lord LLP; Peter J. Fallon (57) ABSTRACT The present invention provides an external preparation for skin which contains 5-aminolevulinic acids as active components and which is excellent in skin-beautifying effects such as prevention/amelioration of skin roughness, dry skin, wrinkles, sagging and flecks of skin, and improvement of turnover of corneum; and in an ameliorating effect on skin diseases such as atopic dermatitis. An external preparation for skin which contains one or more compounds selected from the group consisting of 5-aminolevulinic acid, its salt and a derivative of them; and an iron compound; as active components, is used.

9 Claims, 4 Drawing Sheets (56) References Cited

OTHER PUBLICATIONS

English translation of Abstract for Japanese Laid-Open Patent Application No. 2003-040770.
English translation of Abstract for Japanese Laid-Open Patent Application No. 2002-020294.
English translation of Abstract for Japanese Laid-Open Patent Application No. 07-010750, (1995).
English translation of Abstract for Japanese Laid-Open Patent Application No. 02-108612, (1990).
English translation of Abstract for Japanese Laid-Open Patent Application No. 02-056409, (1990).
English translation of Abstract for Japanese Laid-Open Patent Application No. 2000-290135.
Examination Report issued in New Zealand on Sep. 2, 2010 for a counterpart patent application No. 587593.
New Zealand IP Database Extract available at (www.iponz.govt.nz) for NZ Patent Application No. 550853.
C.A. Rebeiz et al., "Photodynamic herbicides: 1. Concept and phenomenology," Enzyme Microb. Technol., pp. 390-401, vol. 6, (Sep. 1984).
W.E. Grant et al., Abstract of "Photodynamic Therapy of Oral Cancer: Photosensitisation with Systemic Aminolaevulinic Acid," pp. 1-4; Source: Lancet, pp. 147-148; vol. 342 Issue 8864 (Jul. 17, 1993).
Communication from the European Patent Office with Supplementary Partial European Search Report dated Jun. 15, 2015.
Amy Forman Taub, "Photodynamic Therapy in Dermatology: History and Horizons," J. Drugs Dermatol, pp. S8-S25, vol. 3:1 (Jan.-Feb. 2004).
J. Thomas Pento, "Photodynamic Therapy Antineoplastic Agent for Actinic Keratoses Antiacne," Drugs of the Future, pp. 11-17, vol. 22:1 (Jan. 1997).
Extended European Search Report dated Oct. 20, 2015.

* cited by examiner

FIG. 4 though it has been known that 5-aminolevulinic acids are
EXTERNAL PREPARATION FOR SKIN This application is a divisional application of U.S. patent application Ser. No. 11/912,433, filed Oct. 24, 2007, which is national phase entry of International Application No. PCT/JP2005/017681, filed Sep. 27, 2005, which claims priority benefit of Japanese Application No. JP 2005-131171 filed Apr. 28, 2005, the contents of each of which are incorporated in their entireties.

TECHNICAL FIELD

The present invention relates to an external preparation for skin which is excellent in skin-beautifying effects such as prevention/amelioration of skin roughness, dry skin, wrinkles, sagging and flecks of skin, and improvement of turnover of corneum, and an external preparation for skin which is excellent in an ameliorating effect on skin diseases such as atopic dermatitis, more particularly, to an external preparation for skin wherein 5-aminolevulinic acids and an iron compound are used in combination.

BACKGROUND ART

Conventionally, external preparations for skin have been developed, which focused on prevention and amelioration of skin roughness. Examples of such external preparations for skin include: skin external preparations of ameliorating skin roughness which contains alum, calcium salt and magnesium salt (see Japanese Laid-open Patent Application No. 2004-284962), and an agent for preventing/ameliorating skin roughness which consists of N-α-benzoyl-L-arginine, N-α-benzoyl-L-arginine ethyl ester or salt of N-α-benzoyl-L-arginine ethyl ester (see Japanese Laid-open Patent Application No. 2000-281556).

In addition, it has been known that 5-aminolevulinic acids are used as herbicides (for example, see Japanese Laid-open Patent Application No. 08-081322), plant growth regulators (for example, see Japanese Laid-open Patent Application No. 07-53487), external preparations for head (for example, see Japanese Laid-open Patent Application No. 11-116446), etc.

However, an external preparation for skin for making beautiful skin which contains 5-aminolevulinic acids and the effects of 5-aminolevulinic acids on skin roughness, etc., have not been known.

Patent Document 1: Japanese Laid-open Patent Application No. 2004-284962
Patent Document 2: Japanese Laid-open Patent Application No. 2000-281556
Patent Document 3: Japanese Laid-open Patent Application No. 08-081322
Patent Document 4: Japanese Laid-open Patent Application No. 07-53487
Patent Document 5: Japanese Laid-open Patent Application No. 11-116446

DISCLOSURE OF THE INVENTION

An Object to be Attained by the Invention

Though it has been known that 5-aminolevulinic acids are used as herbicides, plant growth regulators, external preparations for head, etc., an external preparation for skin for making beautiful skin which contains 5-aminolevulinic acids and the effects of 5-aminolevulinic acids on skin roughness, etc., have not been known. The object of the present invention is to provide an external preparation for skin which contains 5-aminolevulinic acids as active components and having excellent skin-beautifying effects such as prevention/amelioration of skin roughness, dry skin, wrinkles, sagging and flecks of skin, and improvement of turnover of corneum; and an ameliorating effect on skin diseases such as atopic dermatitis.

Means for Attaining the Object

Conventionally known external preparations for head (hair restorers) containing 5-aminolevulinic acids as active components cannot be used stably because of the following reasons: they cause damages to hair when they are not used in accordance with the direction of their dosage and administration, resulting in problems such as split ends and a decrease in the number of hairs, and in addition, light shielding at the point of use is an absolute requirement. The present inventor has already found that these problems can be avoided by using 5-aminolevulinic acids and iron compounds in combination.

The present inventor has conducted a keen study and found out that a mixture of 5-aminolevulinic acids and iron compounds have: skin-beautifying effects such as prevention/amelioration of skin roughness, dry skin, wrinkles, sagging and flecks of skin, and improvement of turnover of corneum; and an ameliorating effect on skin diseases such as atopic dermatitis. The present invention has been thus completed.

In other words, the present invention relates to: ("1") an external preparation for skin which contains one or more compounds selected from the group consisting of 5-aminolevulinic acid, its salt and a derivative of them; and an iron compound; as active components; ("2") the external preparation for skin according to ("1") mentioned above, which further contains urea as an active component; and the ("3") the external preparation for skin according to ("1") or ("2") mentioned above, wherein the iron compound is one or more compounds selected from the group consisting of ferrous citrate, iron sodium citrate, iron ammonium citrate, iron acetate, iron oxalate, ferrous succinate, iron and sodium succinate citrate, ferrous pyrophosphate, ferric pyrophosphate, heme iron, iron dextran, iron lactate, ferrous gluconate, iron sodium diethylenetriaminepentaacetate, iron ammonium diethylenetriaminepentaacetate, iron sodium ethylenediaminetetraacetate, iron ammonium ethylenediaminetetraacetate, iron triethylenetetraamine, iron sodium dicarboxymethylglutamate, and iron ammonium dicarboxymethylglutamate.

The present invention also relates to: ("4") a preventive/ameliorating drug for skin roughness which contains one or more compounds selected from the group consisting of 5-aminolevulinic acid, its salt and a derivative of them; and an iron compound; as active components; and ("5") the preventive/ameliorating drug for skin roughness according to ("4") mentioned above, wherein one or more compounds selected from the group consisting of ferrous citrate, iron sodium citrate, iron ammonium citrate, iron acetate, iron oxalate, ferrous succinate, iron and sodium succinate citrate, ferrous pyrophosphate, ferric pyrophosphate, heme iron, iron dextran, iron lactate, ferrous gluconate, iron sodium diethylenetriaminepentaacetate, iron ammonium diethylenetriaminepentaacetate, iron sodium ethylenediaminetetraacetate, iron ammonium ethylenediaminetetraacetate, iron triethylenetetraamine, iron sodium dicarboxymethylglutamate, and iron ammonium dicarboxymethylglutamate, are used as an iron compound.

The present invention further relates to: ("6") a preventive/ameliorating drug for dry skin which contains one or more compounds selected from the group consisting of 5-aminolevulinic acid, its salt and a derivative of them; and an iron compound; as active components; and ("7") the preventive/ameliorating drug for dry skin according to ("6") mentioned above, wherein one or more compounds selected from the group consisting of ferrous citrate, iron sodium citrate, iron ammonium citrate, iron acetate, iron oxalate, ferrous succinate, iron and sodium succinate citrate, ferrous pyrophosphate, ferric pyrophosphate, heme iron, iron dextran, iron lactate, ferrous gluconate, iron sodium diethylenetriaminepentaacetate, iron ammonium diethylenetriaminepentaacetate, iron sodium ethylenediaminetetraacetate, iron ammonium ethylenediaminetetraacetate, iron triethylenetetraamine, iron sodium dicarboxymethylglutamate, and iron ammonium dicarboxymethylglutamate, are used as an iron compound.

The present invention also relates to: ("8") a preventive/ameliorating drug for wrinkles/flecks which contains one or more compounds selected from the group consisting of 5-aminolevulinic acid, its salt and a derivative of them; and an iron compound; as active components; and ("9") the preventive/ameliorating drug for wrinkles/flecks according to ("8") mentioned above, wherein one or more compounds selected from the group consisting of ferrous citrate, iron sodium citrate, iron ammonium citrate, iron acetate, iron oxalate, ferrous succinate, iron and sodium succinate citrate, ferrous pyrophosphate, ferric pyrophosphate, heme iron, iron dextran, iron lactate, ferrous gluconate, iron sodium diethylenetriaminepentaacetate, iron ammonium diethylenetriaminepentaacetate, iron sodium ethylenediaminetetraacetate, iron ammonium ethylenediaminetetraacetate, iron triethylenetetraamine, iron sodium dicarboxymethylglutamate, and iron ammonium dicarboxymethylglutamate, are used as an iron compound.

The present invention further relates to: ("10") a method for preventing/ameliorating skin roughness comprising administering transdermally an external preparation for skin which contains one or more compounds selected from the group consisting of 5-aminolevulinic acid, its salt and a derivative of them; and an iron compound; as active components.

The present invention also relates to: ("11") a method for preventing/ameliorating dry skin comprising administering transdermally an external preparation for skin which contains one or more compounds selected from the group consisting of 5-aminolevulinic acid, its salt and a derivative of them; and an iron compound; as active components.

The present invention further relates to: ("12") a method for preventing/ameliorating wrinkles/flecks comprising administering transdermally an external preparation for skin which contains one or more compounds selected from the group consisting of 5-aminolevulinic acid, its salt and a derivative of them; and an iron compound; as active components.

The present invention also relates to: ("13") an ameliorating drug for atopic dermatitis which contains one or more compounds selected from the group consisting of 5-aminolevulinic acid, its salt and a derivative of them; and an iron compound; as active components; and ("14") the ameliorating drug for atopic dermatitis according to ("13") mentioned above, wherein one or more compounds selected from the group consisting of ferrous citrate, iron sodium citrate, iron ammonium citrate, iron acetate, iron oxalate, ferrous succinate, iron and sodium succinate citrate, ferrous pyrophosphate, ferric pyrophosphate, heme iron, iron dextran, iron lactate, ferrous gluconate, iron sodium diethylenetriaminepentaacetate, iron ammonium diethylenetriaminepentaacetate, iron sodium ethylenediaminetetraacetate, iron ammonium ethylenediaminetetraacetate, iron triethylenetetraamine, iron sodium dicarboxymethylglutamate, and iron ammonium dicarboxymethylglutamate, are used as an iron compound.

The present invention further relates to: ("15") a method for ameliorating atopic dermatitis comprising administering transdermally an external preparation for skin which contains one or more compounds selected from the group consisting of 5-aminolevulinic acid, its salt and a derivative of them; and an iron compound; as active components.

The present invention also relates to: ("16") a set of external preparations for skin consisting of a first agent which contains one or more compounds selected from the group consisting of 5-aminolevulinic acid, its salt and a derivative of them, and a second agent which contains an iron compound; ("17") the set of external preparations for skin according to ("16") mentioned above, wherein the first agent and/or the second agent further contain urea; and ("18") the set of external preparations for skin according to ("16") or ("17") mentioned above, wherein the iron compound is one or more compounds selected from the group consisting of ferrous citrate, iron sodium citrate, iron ammonium citrate, iron acetate, iron oxalate, ferrous succinate, iron and sodium succinate citrate, ferrous pyrophosphate, ferric pyrophosphate, heme iron, iron dextran, iron lactate, ferrous gluconate, iron sodium diethylenetriaminepentaacetate, iron ammonium diethylenetriaminepentaacetate, iron sodium ethylenediaminetetraacetate, iron ammonium ethylenediaminetetraacetate, iron triethylenetetraamine, iron sodium dicarboxymethylglutamate, and iron ammonium dicarboxymethylglutamate.

The present invention further relates to: ("19") a method for preventing/ameliorating skin roughness comprising administering transdermally a first agent which contains one or more compounds selected from the group consisting of 5-aminolevulinic acid, its salt and a derivative of them, and a second agent which contains an iron compound; ("20") a method for preventing/ameliorating dry skin comprising administering transdermally a first agent which contains one or more compounds selected from the group consisting of 5-aminolevulinic acid, its salt and a derivative of them, and a second agent which contains an iron compound; ("21") a method for preventing/ameliorating wrinkles/flecks comprising administering transdermally a first agent which contains one or more compounds selected from the group consisting of 5-aminolevulinic acid, its salt and a derivative of them, and a second agent which contains an iron compound; and ("22") a method for ameliorating atopic dermatitis comprising administering transdermally a first agent which contains one or more compounds selected from the group consisting of 5-aminolevulinic acid, its salt and a derivative of them, and a second agent which contains an iron compound.

BRIEF DESCRIPTION OF DRAWINGS

FIG. 1 is a photograph showing an example of clinical testing of an external preparation for skin of the present invention. The photograph was taken 5 days after the start of the treatment with the formulation example 1. As to the treated cheek (the cheek on the left side of FIG. 1), the skin became resilient and dry skin was ameliorated in comparison to the cheek without treatment (the cheek on the right side of FIG. 1). In addition, the treated cheek (the cheek on the left side of FIG. 1) was lifted up in comparison to the cheek without treatment (the cheek on the right side of FIG. 1).

BEST MODE OF CARRYING OUT THE INVENTION

The external preparation for skin of the present invention is not particularly limited as long as it contains one or more compounds selected from the group consisting of 5-aminolevulinic acid, its salt and a derivative of them, and an iron compound, as active components. The above-mentioned 5-aminolevulinic acid is also referred to as δ-aminolevulinic acid, and is one of the amino acids shown by the formula HOOC—$(CH_2)_2$—(CO) $CH_2$—$NH_2$ (hereinafter, also referred to as 5-ALA). This 5-aminolevulinic acid is widely distributed in various organisms, and is generally biosynthesized by 5-aminolevulinic acid synthetase from succinyl CoA and glycine. This 5-aminolevulinic acid is also known as an intermediate of porphyrin biosynthesis.

Examples of salts of 5-aminolevulinic acid of the present invention include acid addition salts such as hydrochloride, phosphate, nitrate, sulfate, acetate, propionate, butylate, valerate, citrate, fumarate, maleate, and malate; and metal salts such as sodium salt, potassium salt, and calcium salt. It is preferred that these salts are used as aqueous solutions, suspensions, or powders at the point of use, and have a same effect as that of 5-aminolevulinic acid.

As a representative embodiment of 5-aminolevulinic acid Derivatives used as active components of the external preparation for skin and the set of external preparations for skin of the present invention, 5-aminolevulinic acid ester and N-acyl-5-aminolevulinic acid are exemplified. As an embodiment of 5-aminolevulinic acid ester, the followings are exemplified: optionally substituted linear, branched or cyclic alkyl ester having 1 to 24 carbon atoms, preferably, for example, an 5-aminolevulinic acid ester whose ester residue is a methyl group, an ethyl group, an isopropyl group, an n-hexyl group, a cyclohexyl group, an n-heptyl group, an n-octyl group, an n-nonyl group, an n-dodecyl group, an n-hexadecyl group, a benzyl group, a phenethyl group, a 3-phenylpropyl group, a hydroxyethyl group, or an ethoxyethyl group. In addition, the followings are exemplified as a substituent of these alkyl groups: a hydroxyl group, an alkoxy group, a phenyl group, a benzyl group, or a hydroxymethyl group. Further, as N-acyl-5-aminolevulinic acid, a compound wherein an amino group of 5-aminolevulinic acid is acylated with, for example, an alkanoyl group, an aromatic acyl group, a benzyloxycarbonyl group or the like, each having 1 to 24 carbon atoms is exemplified. Still further, as a preferred embodiment of an N-acyl group, the followings are specifically exemplified: an acetyl group, an n-pentanoyl group, an n-hexanoyl group, an n-nonanoyl group, a benzoyl group, and a benzyloxycarbonyl group.

The ester of 5-aminolevulinic acid and N-acyl-5-aminolevulinic acid can be produced by publicly known chemical synthesis methods such as methods described in Japanese Laid-open Patent Application No. 4-9360, for example. In addition to chemical synthesis, they can be produced by production methods either by microorganisms or by enzymes. Further, a roughly-purified product containing an object obtained in the process of the production can also be used without separation and purification as long as the roughly-purified product does not contain a toxic substance. Each of 5-aminolevulinic acid, its salt, and their derivatives may be used alone, or by mixing two or more of them. The total amount of 5-aminolevulinic acid, its salt, or a derivative of them contained in the external preparation for skin of the present invention is usually 0.01 to 40 wt %, preferably 0.1 to 10 wt % based on the whole of the external preparation for skin.

The iron compound in the present invention is not particularly limited as long as it is a compound having iron in its molecule. Examples of the iron compound include ferrous citrate, iron sodium citrate, iron ammonium citrate, iron acetate, iron oxalate, ferrous succinate, iron and sodium succinate citrate, ferrous pyrophosphate, ferric pyrophosphate, heme iron, iron dextran, iron lactate, ferrous gluconate, iron sodium diethylenetriaminepentaacetate, iron ammonium diethylenetriaminepentaacetate, iron sodium ethylenediaminetetraacetate, iron ammonium ethylenediaminetetraacetate, iron triethylenetetraamine, iron sodium dicarboxymethylglutamate, iron ammonium dicarboxymethylglutamate, iron choline citrate, ferrous formate, ferric formate, ferric ammonium potassium oxalate, ferrous sulfate, ferric sulfate, iron ammonium sulfate, ferric carbonate, ferrous chloride, ferric chloride, ferric pyrophosphate, and iron oxide. Among them, iron sodium diethylenetriaminepentaacetate and iron ammonium diethylenetriaminepentaacetate are preferred. Each of these iron compounds may be used alone, or by mixing two or more of them. The total amount of the iron compound contained in the external preparation for skin of the present invention is usually 0.01 to 80 wt %, preferably 0.5 to 50 wt % based on the whole of the external preparation for skin.

The external preparation for skin of the present invention acts on sebaceous glands of the skin, and promote the secretion of sebum. Further, the external preparation for skin of the present invention acts on epidermal cells and corneocytes, and activate these cells. It is considered that, as a result of that, it exerts skin-beautifying effects such as prevention/amelioration of skin roughness, dry skin, wrinkles, sagging and flecks of skin, and improvement of turnover of corneum. Therefore, the external preparation for skin of the present invention can be used as a preventive/ameliorating drug for skin roughness, a preventive/ameliorating drug for dry skin, and a preventive/ameliorating drug for wrinkles/flecks. The term "preventive/ameliorating drug" in the preventive/ameliorating drug for skin roughness, the preventive/ameliorating drug for dry skin, and the preventive/ameliorating drug for wrinkles/flecks of the present invention means "preventive and/or ameliorating drug". In addition, the term "wrinkles/flecks" of the present invention means "wrinkles and/or flecks".

Further, the external preparation for skin of the present invention has an ameliorating effect on skin diseases such as atopic dermatitis, eczema and dyskeratosis, as well. More specifically, it has an ameliorating effect on dryness of the skin, pigmentation of the skin, itching of the skin, etc., caused by skin diseases such as atopic dermatitis, eczema and dyskeratosis. Therefore, the external preparation for skin of the present invention can be used as an ameliorating drug for the skin diseases such as atopic dermatitis, eczema and dyskeratosis.

With regard to the external preparation for skin of the present invention, it is not essential that urea is contained therein, however, those further containing urea as an active component are preferred. Urea is a colorless to white crystal or crystalline powder, and is freely soluble in water, soluble in ethanol, and can be formed into many kinds of dosage forms such as lotions and creams, as external preparations. In addition, urea has a high affinity for the skin, and therefore, it has a suitable property as a component of external preparations for skin. Though it depends on the base material and other components used in combination, it is possible to blend urea into the external preparation for skin of the present invention at a ratio of 0.01 to 40 (W/W %; weight ratio), preferably 0.1 to 10%. Commercially available urea can be used directly in applications.

The set of external preparations for skin of the present invention consists of a first agent which contains one or more compounds selected from the group consisting of 5-aminolevulinic acid, its salt and a derivative of them, and a second agent which contains an iron compound. By separating the first agent containing 5-aminolevulinic acid, etc., and the second agent containing an iron compound, the activity of 5-aminolevulinic acid, etc. will last longer. Though the amount of 5-aminolevulinic acid, its salt or a derivative of them contained in the first agent is not particularly limited, the total amount is usually 0.01 to 40 wt %, preferably 0.1 to 10 wt % based on the whole of the first agent. Though the amount of the iron compound contained in the second agent is not particularly limited, the total amount is usually 0.01 to 80 wt %, preferably 0.5 to 50 wt % based on the whole of the second agent.

Further, when the first agent and the second agent of the set of external preparations for skin of the present invention are used in combination, a same effect as in the external preparation for skin of the present invention is obtained. Therefore, the set of external preparations for skin of the present invention can be used as a set of preventive/ameliorating drugs for skin roughness, a set of preventive/ameliorating drugs for dry skin, a set of preventive/ameliorating drugs for wrinkles/flecks, and a set of ameliorating drugs for skin diseases such as atopic dermatitis, eczema and dyskeratosis.

With regard to the first agent and/or the second agent of a set of external preparations for skin of the present invention, it is not essential that urea is further contained therein, however, it is preferred that urea is further contained therein. The amount of urea contained in the first agent and the second agent is not particularly limited, and it is possible to blend urea at a ratio of 0.01 to 40 (W/W %; weight ratio), preferably 0.1 to 10%.

In addition to 5-aminolevulinic acid, its salt or a derivative of them, an iron compound and urea mentioned above, one or more of various components commonly used in pharmaceuticals and cosmetics, in other words, aqueous components, oily components, powdery components, chemical agents such as surface active agents, moisturizing agents, thickeners, colorants, fragrances, pH adjusters, antioxidants, antiseptics, or UV protectants, and anti-inflammatory agents can be blended into the external preparation for skin of the present invention, and the first agent and the second agent of the set of external preparations for skin of the present invention, to the extent that they do not damage the effect of the present invention.

As aqueous components, for example, water, lower alcohol (methanol, ethanol, denatured ethanol, propanol, isopropyl alcohol), etc., are exemplified.

As the oily components, for example, higher fatty acids (stearic acid, palmitic acid, myristic acid, lauric acid and esters thereof, etc.), higher alcohols (cetanol, lanolin alcohol, stearyl alcohol, cetostearyl alcohol, etc.) and waxes (hard paraffin, microcrystalline wax, ceresin wax, polyethylene wax, beeswax, Japan wax, carnauba wax, candelilla wax, etc.), natural or synthetic oily substances (squalane, liquid paraffin, lanolin or derivatives thereof, olive oil, camellia oil, cottonseed oil, oleyl alcohol, castor oil, Vaseline, diethoxyethyl adipate ester, silicon oil, fluorine oil, etc.) are exemplified.

As powdery components, for example, aluminum powders, titanium oxide powders, zinc oxide powders, iron oxide powders, acrylic powders, silica beads, talc, sericite, etc., are exemplified.

As surface active agents, for example, sorbitan fatty acid ester, glycerine fatty acid ester, polyglycerine fatty acid ester, propylene glycol fatty acid ester, polyoxyethylene sorbitan fatty acid ester, polyoxyethylene sorbit fatty acid ester, polyoxyethylene glycerine fatty acid ester, polyethylene glycol fatty acid ester, polyoxyethylene alkyl ether, polyoxyethylene polyoxypropylene alkyl ether, polyoxyethylene alkylphenyl ether, polyoxyethylene hydrogenated castor oil, polyoxyethylene castor oil, polyoxyethylene beeswax derivatives, polyoxyethylene lanolin derivatives, polyoxyethylene alkylamide, polyoxyethylene alkylamine, lecithin derivatives, polymeric emulsifiers, etc., are exemplified.

As moisturizing agents, for example, polyhydric alcohols such as glycerine, propylene glycol, 1,3-butylene glycol, dipropylene glycol, ethylene glycol, 1,4-butylene glycol, diglycerine, triglycerine, sorbit or derivatives thereof, polyethylene glycol, etc.; and glucose, maltose, maltitol, sucrose, fructose, threitol, erythritol, sorbit, starch-degraded sugar, hyaluronic acid, chondroitin sulfate, hydrolyzed collagen, hydrolyzed elastin, carboxymethyl chitin, casein soda, muchin, glycosphingolipid, etc., are exemplified.

As thickeners, for example, carboxyvinyl polymer, CP jelly, carboxymethyl cellulose, carageenan, sodium alginate, bentonite, veegum, synthetic hectorite, etc., are exemplified.

As antioxidants, for example, butylated hydroxytoluene (BHT), butylated hydroxyanisole (BHA), sodium pyrosulfite, sodium bisulfate, tocopherol, sodium edetate, ascorbic acid, isopropyl gallate, etc., are exemplified.

As pH adjusters, for example, citric acid, lactic acid, tartaric acid, phosphoric acid, etc., are exemplified.

As antihistamines, for example, diphenhydramine hydrochloride, isothipendyl hydrochloride, etc., are exemplified.

As antiseptics, for example, methyl, ethyl, propyl, and butyl esters of p-hydroxybenzoic acid, phenoxyethanol, o-phenylphenol, dehydroacetic acid or salts thereof, p-cresol, m-cresol, o-chlor-m-xylenol, etc., are exemplified.

As UV protectants, for example, ascorbic acid or derivatives thereof, isoferulic acid or salts thereof, oxybenzone or derivatives thereof, p-aminobenzoic acid or derivatives thereof, urocanic acid or derivatives thereof, kojic acid, dibenzoyl methane or derivatives thereof, p-methoxycinnamic acid or derivatives thereof, particulate titanium oxide, particulate zinc oxide, particulate iron oxide, etc., are exemplified.

As anti-inflammatory agents, for example, glycyrrhetinic acid or derivatives thereof, glycyrrhizinic acid or derivatives thereof, guaiazulene or derivatives thereof, bisabolol, geraniin, horse chestnut extracts, aloe extracts, etc., are exemplified.

Each of the components and the chemical agents mentioned above can be used alone, or by mixing two or more of them.

With regard to the dosage form of an external preparation for skin of the present invention, and of the first agent and the second agent of the set of external preparations for skin of the present invention, any form of powders, liquids and ointments can be employed. Dosage forms such as lotions, emulsions, creams (ointments), gels, and aerosols can be prepared, according to methods usually used (for example, methods prescribed in The Japanese Pharmacopoeia $12^{th}$ Edition). Further, the external preparation for skin of the present invention may be liposomally encapsulated. Methods for liposomal encapsulation are not particularly limited, and are described, for example, in Japanese Laid-open Patent Application No. 11-199488, etc.

When prepared as aqueous solutions such as lotions, or creams (ointments), in order to prevent degradation of 5-aminolevulinic acid or its salt or a derivative of them, it is preferred to prepare the external preparation for skin while paying attention not to cause alkalinization. In case of alkalinization, degradation can be prevented by removing oxygen. Paying attention to this, 5-aminolevulinic acid or its salt or a derivative of them can be used in combination with components of liquids or ointments usually used.

Though there is no particular limitation to the method for using an external preparation for skin of the present invention, it is preferred that the external preparation for skin of the present invention is transdermally administered to the skin by methods such as spraying, application, or a poultice. In addition, transdermal administration using a drug delivery system such as iontophoresis is preferred because it promotes the speed of drug absorption into skin tissues and increases the ratio of drug absorption, as well.

There is no particular limitation to the method for using a set of external preparations for skin of the present invention, and the following methods can be adapted: a method comprising mixing the first agent and the second agent together, and applying the mixture to the skin; a method comprising applying the first agent and the second agent to the skin at the same time; a method comprising applying the first agent to the skin and then applying the second agent to the same part; and a method comprising the second agent to the skin and then applying the first agent to the same part. Further, though the method comprising administering the first agent and the second agent is not particularly limited, methods such as spraying, application, or a poultice to the skin, or methods using a drug delivery system such as iontophoresis are preferred.

With regard to the dosage of the external preparation for skin of the present invention, and the first agent and the second agent of the set of external preparations for skin of the present invention, there is no particular limitation as long as it is a level exerting an effect on skin roughness etc. However, in case of application to the skin, it is preferred to administer the external preparation for skin such that 5-aminolevulinic acid or its salt and a derivative of them is administered in an amount of 10 μg to 10 mg, desirably 100 μg to 5 mg, more desirably 1 mg to 5 mg per 10 $cm^2$ of skin, in 5-aminolevulinic acid hydrochloride equivalent. The dosage of iron compounds to be combined with 5-aminolevulinic acid, etc., is 50 μg to 50 mg, desirably 500 μg to 25 mg, more desirably 5 mg to 25 mg, in iron equivalent under the same conditions.

As an administration form of the external preparation for skin of the present invention, and of the first agent and the second agent of the set of external preparations for skin of the present invention, the following method is preferably exemplified but not limited thereto: a method comprising administering transdermally the external preparation for skin of the present invention, or the first agent and the second agent of the set of external preparations for skin of the present invention from the twilight to the night by methods such as application, and rinsing off in the same night.

One characteristic of the external preparation for skin and the set of external preparations for skin of the present invention resides in the point that there is no need for a strict light shielding treatment, which is necessary when 5-aminolevulinic acid is administered (application, etc.) alone. However, it is preferred to avoid being exposed to strong light, for example, being in a scorching sun. With the use of the external preparation for skin and the set of external preparations for skin of the present invention, in many cases, skin-beautifying effects such as amelioration of skin roughness, dry skin, wrinkles, sagging and flecks of skin, and improvement of turnover of corneum, and an ameliorating effect on skin diseases such as atopic dermatitis are seen from day 3. In case the effects reach a plateau, the effects can be expected again by stopping the administration once and resuming the administration 3 months later, though the external preparation for skin and the set of external preparations for skin of the present invention can be used continuously.

The methods of the present invention are: a method for preventing/ameliorating skin roughness comprising administering transdermally an external preparation for skin which contains one or more compounds selected from the group consisting of 5-aminolevulinic acid, its salt and a derivative of them; and an iron compound; as active components; a method for preventing/ameliorating dry skin comprising administering transdermally an external preparation for skin which contains one or more compounds selected from the group consisting of 5-aminolevulinic acid, its salt and a derivative of them; and an iron compound; as active components; a method for preventing/ameliorating wrinkles/flecks comprising administering transdermally an external preparation for skin which contains one or more compounds selected from the group consisting of 5-aminolevulinic acid, its salt and a derivative of them; and an iron compound; as active components; a method for ameliorating atopic dermatitis comprising administering transdermally an external preparation for skin which contains one or more compounds selected from the group consisting of 5-aminolevulinic acid, its salt and a derivative of them; and an iron compound; as active components; a method for preventing/ameliorating skin roughness comprising administering transdermally a first agent which contains one or more compounds selected from the group consisting of 5-aminolevulinic acid, its salt and a derivative of them, and a second agent which contains an iron compound; a method for preventing/ameliorating dry skin comprising administering transdermally a first agent which contains one or more compounds selected from the group consisting of 5-aminolevulinic acid, its salt and a derivative of them, and a second agent which contains an iron compound; a method for preventing/ameliorating wrinkles/flecks comprising administering transdermally a first agent which contains one or more compounds selected from the group consisting of 5-aminolevulinic acid, its salt and a derivative of them, and a second agent which contains an iron compound; and a method for ameliorating atopic dermatitis comprising administering transdermally a first agent which contains one or more compounds selected from the group consisting of 5-aminolevulinic acid, its salt and a derivative of them, and a second agent which contains an iron compound. There is no particular limitation to the method for transdermally administering the first agent and the second agent mentioned above, and the following methods can be adapted: a method comprising mixing the first agent and the second agent together, and applying the mixture to the skin; a method comprising applying the first agent and the second agent to the skin at the same time; a method comprising applying the first agent to the skin and applying the second agent to the same part; and a method comprising applying the second agent to the skin and then applying the first agent to the same part.

The present invention will be described more specifically with reference to the Examples, however, the technical scope of the present invention is not limited to these exemplifications.

EXAMPLE 1

1.5 g of 5-aminolevulinic acid hydrochloride, 3 g of urea and 1 g of ferrous citrate were mixed well into 20 ml of purified water in which 4% of 1,3-butylene glycol and 0.15% of methylparaben had been dissolved, to prepare the formulation example 1 was prepared.

About 2 ml of the formulation example 1 was applied every night to faces of subjects (8 adult women). After application, the faces were left for 30 minutes to 1 hour, and then the faces were washed in the same night, to rinse off the formulation example.

The conventional strict light shielding conditions, applied when 5-aminolevulinic acids are used alone, were not performed, and hair removal occurring when the dosage is partially excessive was not observed. The formulation example 1 was evaluated 5 days after the start of the application by each of 8 subjects. The results are shown below.

Figure 1:
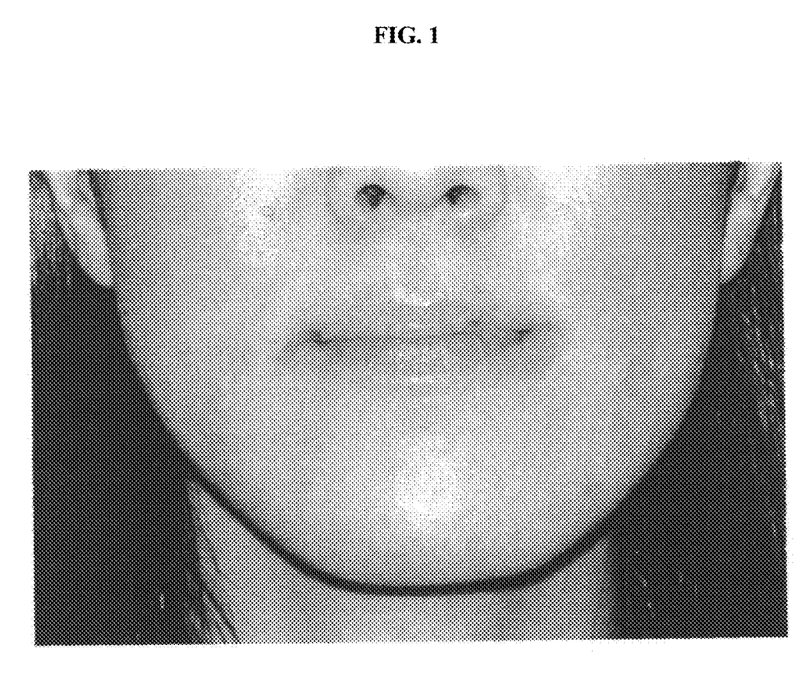

Subject 1: only the right half of the face was treated with the formulation example 1, and the skin at the treated part became resilient and the dryness was ameliorated. In addition, the treated cheek (the cheek on the left side of FIG. 1) was lifted up in comparison to the cheek without treatment.

Subject 2: the skin became resilient. The nasolabial folds that run from the nose to the both sides of the mouth became less prominent. When the formulation example 1 was being applied longer, the secretion of sebum increased, and dry skin was ameliorated. Makeup was put on in a better state.

Subject 3: the skin became resilient. The nasolabial folds became less prominent. Crow's feet disappeared. Makeup was put on in a better state.

Subject 4: the skin became resilient. The complexion became fairer.

Subject 5: the skin became resilient. Dry skin was ameliorated. Makeup was put on in a better state.

Subject 6: the skin became resilient. The skin became moisturized.

Subject 7: there was no special change.

Subject 8: there was no special change.

As described above, 6 out of 8 subjects noticed subjective symptoms showing amelioration of skin condition, for example, skin resilience. As it can be seen from the comment of subject 2, the external preparation for skin of the present invention has an effect on promoting the secretion of sebum, and it is considered that, as a result of that, it exerts effects on improving skin resilience, ameliorating dry skin, and making nasolabial folds less prominent, etc. With regard to subject 1, who is a patient of atopic dermatitis, the skin became resilient and the dryness was ameliorated. Consequently, it is suggested that the external preparation for skin of the present invention is also effective for prevention/amelioration of skin roughness, dry skin, wrinkles, and sagging of skin resulted from atopic dermatitis. In addition, an effect on making complexion fairer, as in the case of subject 4, was observed as well.

EXAMPLE 2

The formulation example 1 in Example 1 was applied once every night to affected areas of 6 patients of atopic dermatitis (subjects 9 to 13; and subject 1 in Example 1), and 2 patients of chronic eczema (subjects 14 to 15) in an amount of about 1 ml per 100 $cm^2$ of skin. After application, the affected areas were left for 30 minutes to 1 hour, and then the areas to which the formulation example 1 was applied were washed in the same night to rinse off the formulation example. The affected areas, 1, 2 weeks after the start of the administration of the formulation example 1, were compared with the affected areas before the administration, and the judgment and the evaluation of "markedly ameliorated" "ameliorated" "no change" and "worsened" were conducted by the inventor, who is a doctor. The judgment and evaluation were conducted using the levels of amelioration of redness, pigmentation and itching of the skin, and the level of softening of the skin, as an indicator. As a result, 4 out of 6 patients of atopic dermatitis were "markedly ameliorated" and the other 2 patients were "ameliorated", and 1 out of 2 patients of chronic eczema was "markedly ameliorated" and the other patient was "ameliorated". Based on this result, it is shown that the external preparation for skin of the present invention ameliorates not only atopic dermatitis but also skin conditions such as eczema and dyskeratosis.

Hereinafter, 3 out of 8 patients of atopic dermatitis will be described in more detail.

Subject 1: "Ameliorated"

Subject 1 has been suffering from atopic dermatitis. Only the right half of the face was treated with the formulation example 1, and the skin at the treated part became resilient and the dryness was ameliorated. In addition, the skin at the treated part became soft and the treated cheek was lifted up in comparison to the cheek without treatment.

Subject 9: "Markedly Ameliorated"

Figure 2:
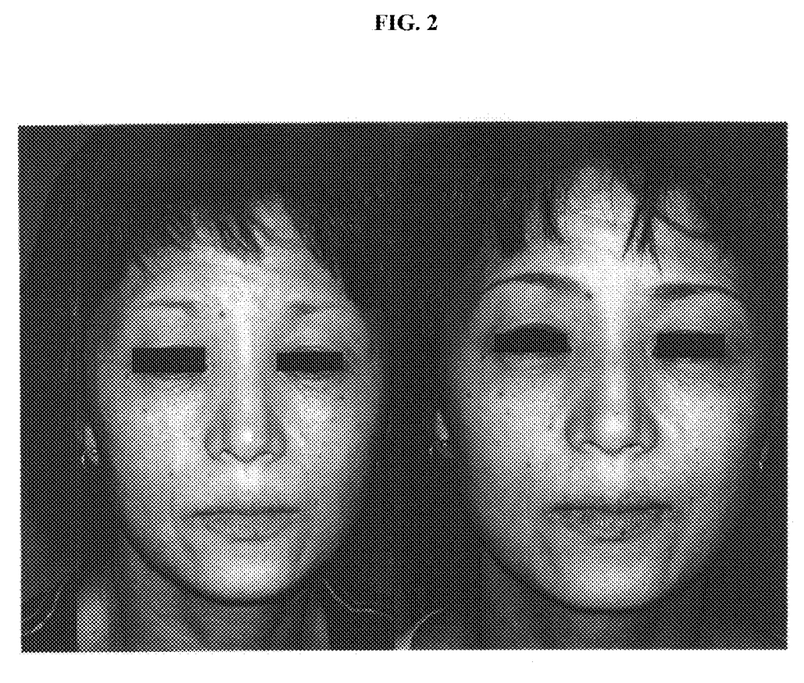
FIG. 2 is a set of photographs showing an example of clinical testing of an external preparation for skin of the present invention. The left photograph is a photograph of the face before the start of the treatment with the formulation example 1, and the right photograph is a photograph of the face 14 days after the start of the treatment with the formulation example 1. After the treatment, the redness and the pigmentation of the affected area are ameliorated in comparison to those before the treatment.

Subject 9 has been suffering from atopic dermatitis since elementary school, and has been using external preparations of steroid intermittently for several decades. Major affected areas are the face and neck. In the affected areas, the skin was hard and exhibited redness and pigmentation (see FIG. 2, the left photograph of the face), and was accompanied by itching, and a typical atopy-like appearance was observed. Subject 9 was instructed to use the formulation example 1 together with an external preparation of steroid, and 3 days later, the external preparation of steroid was discontinued because the itching disappeared. After that, only the formulation example 1 was used, and the redness and pigmentation in the affected areas were ameliorated, and the skin became soft (see FIG. 2, the right photograph of the face). Further, the conditions of wrinkles and flecks of the skin were also ameliorated.

Subject 10: "Markedly Ameliorated"

Figure 3:
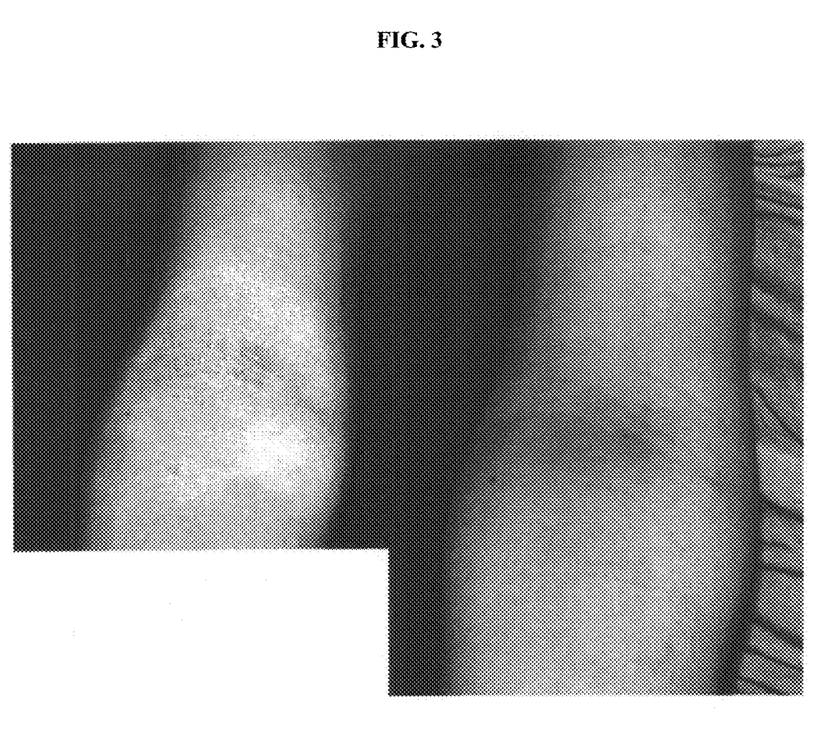
FIG. 3 is a set of photographs showing an example of clinical testing of an external preparation for skin of the present invention. The left photograph is a photograph of the inside of the elbow before the start of the treatment with the formulation example 1, and the right photograph is a photograph of the inside of the elbow 7 days after the start of the treatment with the formulation example 1. After the treatment, the redness and pigmentation of the affected area are ameliorated in comparison to those before the treatment, and the appearance of the skin is nearly normal.
Figure 4:
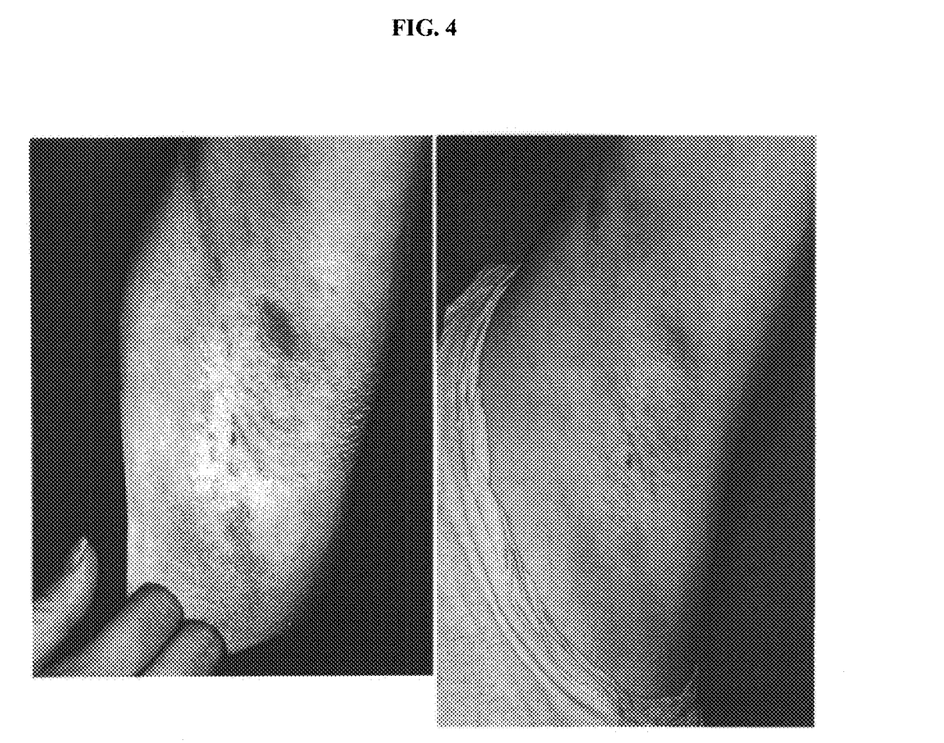
FIG. 4 is a set of photographs showing an example of clinical testing of an external preparation for skin of the present invention. The left photograph is a photograph of the underarm before the start of the treatment with the formulation example 1, and the right photograph is a photograph of the underarm 7 days after the start of the treatment with the formulation example 1. After the treatment, the redness and the pigmentation of the affected area are ameliorated in comparison to those before the treatment, and the appearance of the skin is nearly normal. In addition, no scratches are observed in the photograph after the treatment because the itching subsided.

Subject 10 has been suffering from atopic dermatitis since elementary school, and has been using external preparations of steroid intermittently for several decades. Major affected areas are the underarm and inside of the elbow. In the affected areas, there was itching, and the skin was hard and exhibited redness, pigmentation and scratches [see the left photographs of FIG. 3 (the inside of the elbow) and FIG. 4 (the underarm)], and a typical atopy-like appearance was observed. Subject 10 was instructed to use the formulation example 1 together with an external preparation of steroid, and 3 days later, the external preparation of steroid was discontinued because the itching disappeared. After that, only the formulation example 1 was used, and the redness and pigmentation in the affected areas were ameliorated, the skin became soft and the appearance of the skin became nearly normal [see the right photographs of FIG. 3 (the inside of the elbow) and FIG. 4 (the underarm)].

INDUSTRIAL APPLICABILITY

The external preparation for skin of the present invention which contains 5-aminolevulinic acids has skin-beautifying effects such as prevention/amelioration of skin roughness, dry skin, wrinkles, sagging and flecks of skin, and improvement of turnover of corneum; and an ameliorating effect on dermatitis such as atopic dermatitis. Further, as 5-aminolevulinic acids and an iron compound are used in combination in the external preparation for skin of the present invention, light shielding at the point of use is not an absolute requirement for the external preparation for skin of the present invention and its usage is simple. Moreover, with regard to the skin-beautifying effects such as prevention/amelioration of skin roughness, dry skin, wrinkles, sagging and flecks of skin, and improvement of turnover of corneum; and the ameliorating effect on skin diseases such as atopic dermatitis, the external preparation for skin of the present invention exhibits a remarkable effect equal to or stronger than the effect observed when 5-aminolevulinic acids are used alone.

The invention claimed is:

1. A method for inhibiting progression of or ameliorating skin roughness, dry skin, wrinkles, sagging skin and flecks and/or atopic dermatitis, said method comprising: administering transdermally an external preparation for skin, wherein the external preparation for skin contains
   (A) an iron compound selected from the group consisting of ferrous citrate, iron sodium citrate, iron ammonium citrate, iron acetate, iron oxalate, ferrous succinate, iron and sodium succinate citrate, ferrous pyrophosphate, ferric pyrophosphate, heme iron, iron dextran, iron lactate, ferrous gluconate, iron sodium diethylenetriaminepentaacetate, iron ammonium diethylenetriaminepentaacetate, iron sodium ethylenediaminetetraacetate, iron ammonium ethylenediaminetetraacetate, iron triethylenetetraamine, iron sodium dicarboxymethylglutamate, and iron ammonium dicarboxymethylglutamate in an amount of 0.5 to 50 wt % based on the total weight of the external preparation for skin, and
   (B) 5-aminolevulinic acid, a pharmaceutically acceptable salt of 5-aminolevulinic acid or a pharmaceutically acceptable ester derivative of 5-aminolevulinic acid or the salt thereof in an amount of 0.1 to 10 wt % based on the total weight of the external preparation, wherein each component of the preparation is administered transdermally either simultaneously or immediately sequentially in a same location of the skin.

2. The method according to claim 1, wherein the external preparation for skin further contains urea.

3. The method according to claim 2, wherein the iron compound is ferrous citrate, iron sodium diethylenetriaminepentaacetate, or iron ammonium diethylenetriaminepentaacetate.

4. The method according to claim 1, wherein the iron compound is ferrous citrate, iron sodium diethylenetriaminepentaacetate, or iron ammonium diethylenetriaminepentaacetate.

5. A method according to claim 1 wherein administering transdermally the external preparation for skin comprises
   administering transdermally the component (A), and then administering transdermally the component (B) immediately sequentially in a same location;
   administering transdermally the component (B), and then administering transdermally the component (A) immediately sequentially in a same location; or
   administering transdermally the component (A) and the component (B) simultaneously in a same location.

6. The method according to claim 5, wherein the component (A) and/or the component (B) further contain urea.

7. A method for inhibiting progression of or ameliorating skin roughness, dry skin, wrinkles, sagging skin and flecks and/or atopic dermatitis, said method comprising administering transdermally an external preparation for skin, wherein the external preparation for skin is consists essentially of:
   (A) an iron compound selected from the group consisting of ferrous citrate, iron sodium citrate, iron ammonium citrate, iron acetate, iron oxalate, ferrous succinate, iron and sodium succinate citrate, ferrous pyrophosphate, ferric pyrophosphate, heme iron, iron dextran, iron lactate, ferrous gluconate, iron sodium diethylenetriaminepentaacetate, iron ammonium diethylenetriaminepentaacetate, iron sodium ethylenediaminetetraacetate, iron ammonium ethylenediaminetetraacetate, iron triethylenetetraamine, iron sodium dicarboxymethylglutamate, and iron ammonium dicarboxymethylglutamate in an amount of 0.5 to 50 wt % based on the total weight of the external preparation for skin; and
   (B) 5-aminolevulinic acid, a pharmaceutically acceptable salt of 5-aminolevulinic acid or a pharmaceutically acceptable ester derivative of 5-aminolevulinic acid or the salt thereof in an amount of 0.1 to 10 wt % based on the total weight of the external preparation,
   wherein each component of the preparation is administered transdermally either simultaneously or immediately sequentially in a same location of the skin.

8. A method for inhibiting progression of or ameliorating skin roughness, dry skin, wrinkles, sagging skin and flecks and/or atopic dermatitis, said method comprising administering transdermally an external preparation for skin, wherein the external preparation for skin is consists essentially of
   (a) an iron compound selected from the group consisting of ferrous citrate, iron sodium citrate, iron ammonium citrate, iron acetate, iron oxalate, ferrous succinate, iron and sodium succinate citrate, ferrous pyrophosphate, ferric pyrophosphate, heme iron, iron dextran, iron lactate, ferrous gluconate, iron sodium diethylenetriaminepentaacetate, iron ammonium diethylenetriaminepentaacetate, iron sodium ethylenediaminetetraacetate, iron ammonium ethylenediaminetetraacetate, iron triethylenetetraamine, iron sodium dicarboxymethylglutamate, and iron ammonium dicarboxymethylglutamate in an amount of 0.5 to 50 wt % based on the total weight of the external preparation for skin, (b) 5-aminolevulinic acid, a pharmaceutically acceptable salt of 5-aminolevulinic acid or a pharmaceutically acceptable ester derivative of 5-aminolevulinic acid or the salt thereof is in an amount of 0.1 to 10 wt % based on the total weight of the external preparation, and (c) urea in an amount of 0.1 to 10 w/w % of the total weight of the external preparation, wherein each component of the preparation is administered transdermally either simultaneously or immediately sequentially in a same location of the skin.

9. A method for inhibiting progression of or ameliorating skin roughness, dry skin, wrinkles, sagging skin and flecks and/or atopic dermatitis, said method comprising administering transdermally an external preparation for skin, wherein the external preparation for skin is consists essentially of (a) an iron compound selected from the group consisting of ferrous citrate, iron sodium diethylenetriaminepentaacetate, and iron ammonium diethylenetriaminepentaacetate in an amount of 0.5 to 50 wt % based on the total weight of the external preparation for skin, (b) 5-aminolevulinic acid, a pharmaceutically acceptable salt of 5-aminolevulinic acid or a pharmaceutically acceptable ester derivative of 5-aminolevulinic acid or the salt thereof is in an amount of 0.1 to 10 wt % based on the total weight of the external preparation, and (c) urea in an amount of 0.1 to 10 w/w % of the total weight of the external preparation, wherein each component of the preparation is administered transdermally either simultaneously or immediately sequentially in a same location of the skin.

\* \* \* \* \*